(12) United States Patent
Kuriyama et al.

(10) Patent No.: US 12,161,493 B2
(45) Date of Patent: Dec. 10, 2024

(54) RADIATION IMAGING APPARATUS AND RADIATION IMAGING SYSTEM

(71) Applicant: CANON KABUSHIKI KAISHA, Tokyo (JP)

(72) Inventors: Misaki Kuriyama, Tokyo (JP); Satoru Sawada, Kanagawa (JP); Takanori Taya, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 47 days.

(21) Appl. No.: 17/820,518

(22) Filed: Aug. 17, 2022

(65) Prior Publication Data

US 2023/0061406 A1     Mar. 2, 2023

(30) Foreign Application Priority Data

Aug. 27, 2021  (JP) ................. 2021-138848
Aug. 27, 2021  (JP) ................. 2021-138849

(51) Int. Cl.
    *G01T 1/20*         (2006.01)
    *A61B 6/42*         (2024.01)
    *G01N 23/04*       (2018.01)
    *G01N 23/203*     (2006.01)

(52) U.S. Cl.
CPC .......... *A61B 6/4233* (2013.01); *A61B 6/4283* (2013.01); *G01N 23/04* (2013.01); *G01N 23/203* (2013.01); *G01T 1/20* (2013.01)

(58) Field of Classification Search
None
See application file for complete search history.

(56) References Cited

U.S. PATENT DOCUMENTS

| | | | |
|---|---|---|---|
| 6,433,341 B1 * | 8/2002 | Shoji | H04N 1/32122 250/385.1 |
| 7,053,378 B2 * | 5/2006 | Yamamoto | G01N 23/04 250/370.11 |
| 7,317,190 B2 * | 1/2008 | Ertel | G01T 1/2006 250/517.1 |
| 7,495,226 B2 * | 2/2009 | Jadrich | G01T 1/20 250/370.09 |

(Continued)

FOREIGN PATENT DOCUMENTS

| | | |
|---|---|---|
| JP | 2003014862 A | 1/2003 |
| JP | 2004294114 A | 10/2004 |

*Primary Examiner* — David P Porta
*Assistant Examiner* — Djura Malevic
(74) *Attorney, Agent, or Firm* — Canon U.S.A., Inc. IP Division

(57) ABSTRACT

A radiation imaging apparatus includes an attenuation member on the back surface side opposite the radiation incident surface of a radiation detection unit. The attenuation member is configured to reduce unexpected appearance of a part disposed on the back surface side of the radiation imaging apparatus, the unexpected appearance of which occurs due to backscattered radiation reflected by the structured part on the back surface side of the radiation imaging apparatus. The attenuation member includes a material having a radiation transmittance higher than that of the part and covers the end portion of the outline of the part that overlaps the radiation detection unit in orthogonal projection onto the surface opposite the incident surface of the radiation detection unit, and the area of the attenuation member is smaller than that of the radiation detection unit.

19 Claims, 7 Drawing Sheets

(56) References Cited

U.S. PATENT DOCUMENTS

| | | | | |
|---|---|---|---|---|
| 7,569,831 B2* | 8/2009 | Jadrich | G03B 42/04 | 250/370.11 |
| 7,586,096 B2* | 9/2009 | Astley | G01T 1/17 | 250/370.15 |
| 7,643,611 B2* | 1/2010 | Shedlock | G01V 5/222 | 378/87 |
| 7,663,114 B2* | 2/2010 | Aoyagi | G01T 1/2928 | 250/370.09 |
| 7,812,314 B1* | 10/2010 | Smith | G01T 7/00 | 250/370.09 |
| 7,947,960 B2* | 5/2011 | Wu | G03B 42/02 | 250/370.09 |
| 8,053,727 B2* | 11/2011 | Nishino | A61B 6/56 | 250/336.1 |
| 8,269,182 B2* | 9/2012 | Konkle | G01T 1/244 | 250/370.09 |
| 8,431,902 B2* | 4/2013 | Nakatsugawa | A61B 6/4283 | 250/361 R |
| 8,744,044 B2* | 6/2014 | Suwa | A61B 6/00 | 378/62 |
| 8,796,623 B2* | 8/2014 | Nakatsugawa | G01T 1/20 | 250/336.1 |
| 8,816,291 B2* | 8/2014 | Hawver | G01N 23/203 | 250/370.09 |
| 8,969,820 B2* | 3/2015 | Suwa | A61B 6/4405 | 250/371 |
| 8,981,309 B2* | 3/2015 | Noguchi | G03B 42/04 | 378/177 |
| 9,088,032 B2* | 7/2015 | Jang | H01M 50/591 | |
| 9,104,097 B2* | 8/2015 | Suwa | A61B 6/4283 | |
| 9,168,016 B2* | 10/2015 | Ohta | A61B 6/4405 | |
| 9,380,988 B2* | 7/2016 | Kitano | A61B 6/56 | |
| 9,535,165 B2* | 1/2017 | Takatori | G01T 1/17 | |
| 9,594,033 B2* | 3/2017 | Georgeson | G01T 1/04 | |
| 9,978,234 B2* | 5/2018 | Kano | G01T 1/244 | |
| 10,192,646 B2* | 1/2019 | Lee | G21F 1/085 | |
| 10,605,750 B2* | 3/2020 | Georgeson | G01N 23/203 | |
| 10,631,802 B2* | 4/2020 | Horiuchi | A61B 6/4283 | |
| 10,722,195 B2* | 7/2020 | Suwa | A61B 6/4283 | |
| 11,141,120 B2* | 10/2021 | Sakuragi | A61B 6/4208 | |
| 11,207,048 B2* | 12/2021 | Kim | A61B 6/4452 | |
| 11,253,212 B2* | 2/2022 | Jacob | G01T 1/20182 | |
| 11,774,376 B2* | 10/2023 | Fukushima | G01N 23/04 | 378/62 |
| 2002/0014594 A1* | 2/2002 | Endo | G01T 1/244 | 250/370.09 |
| 2004/0149930 A1* | 8/2004 | Ando | G03B 42/04 | 378/182 |
| 2004/0188626 A1* | 9/2004 | Yamamoto | G01N 23/04 | 250/370.09 |
| 2004/0211909 A1* | 10/2004 | Watanabe | G03B 42/02 | 250/370.11 |
| 2004/0245474 A1* | 12/2004 | Vieux | G01T 1/20 | 250/370.11 |
| 2006/0098788 A1* | 5/2006 | McGovern | G03C 3/003 | 378/169 |
| 2007/0272873 A1* | 11/2007 | Jadrich | G01T 1/20 | 250/370.11 |
| 2008/0078940 A1* | 4/2008 | Castleberry | G01T 1/20189 | 250/370.09 |
| 2012/0074331 A1* | 3/2012 | Koyanagi | G01T 1/16 | 250/394 |
| 2012/0248321 A1* | 10/2012 | Hawver | G01N 23/203 | 250/395 |
| 2013/0082184 A1* | 4/2013 | Nakatsugawa | A61B 6/4266 | 250/361 R |
| 2013/0266121 A1* | 10/2013 | Suwa | A61B 6/4283 | 378/189 |
| 2014/0211921 A1* | 7/2014 | Bandis | H01M 50/24 | 429/96 |
| 2014/0226795 A1* | 8/2014 | Kitano | A61B 6/56 | 378/189 |
| 2015/0293237 A1* | 10/2015 | Suzuki | G03B 42/04 | 250/369 |
| 2016/0299237 A1* | 10/2016 | Kondo | G01T 1/2023 | |
| 2017/0038252 A1* | 2/2017 | Suzuki | G01J 1/4228 | |
| 2017/0090044 A1* | 3/2017 | Suzuki | A61B 6/4283 | |
| 2017/0311913 A1* | 11/2017 | Suzuki | A61B 6/4216 | |
| 2017/0367666 A1* | 12/2017 | Horiuchi | A61B 6/4283 | |
| 2017/0372572 A1* | 12/2017 | Kano | C22C 23/00 | |
| 2018/0110495 A1* | 4/2018 | MacLaughlin | A61B 6/545 | |
| 2019/0008472 A1* | 1/2019 | Tajima | A61B 6/4266 | |
| 2019/0196033 A1* | 6/2019 | Horiuchi | G01T 1/244 | |
| 2019/0293812 A1* | 9/2019 | Suzuki | G01T 7/00 | |
| 2021/0199602 A1* | 7/2021 | Fukushima | G01T 1/20 | |
| 2022/0043169 A1* | 2/2022 | Nomura | G01T 1/20 | |

* cited by examiner

RADIATION IMAGING APPARATUS AND RADIATION IMAGING SYSTEM

BACKGROUND OF THE INVENTION

Field of the Invention

The present invention relates to a radiation imaging apparatus and a radiation imaging system.

Description of the Related Art

Radiation imaging apparatuses use a flat-panel detector (hereinafter abbreviated as "FPD"), made of a semiconductor material, as a radiation detection unit. Radiation imaging apparatuses of this type are in wide spread use as imaging apparatuses for medical diagnostic imaging or nondestructive inspection. For example, in a radiation imaging system, a radiation imaging apparatus is a digital imaging apparatus capable of still image capturing such as general X-ray imaging or moving image capturing such as fluoroscopic imaging in medical diagnostic imaging.

The radiation imaging apparatus uses the FPD disposed inside a housing to convert radiation emitted from a radiation generating apparatus into an electric signal, and converts the electrical signal into digital data that can be used for generating a radiation image. In this process, the emitted radiation can partially pass through the FPD, then be reflected by a structure opposite the side where the radiation is incident on the FPD, get scattered (backscattered radiation), and enter the FPD again. The backscattered radiation can pass through a part on the surface of the FPD opposite the surface of the FPD where the radiation is incident, enter the FPD, through which the part unexpectedly appears in a radiation image as an artifact.

For example, the publication of Japanese Patent Application Laid-Open No. 2004-294114 discusses a technique for reducing the influence of an artifact using attenuation members different in radiation transmittance by region so that the amounts of backscattered radiation reaching an FPD are approximately uniform. Attenuation members have lower radiation transmittance as they get heavier. The technique of the publication of Japanese Patent Application Laid-Open No. 2004-294114, however, uses an attenuation member with a high radiation transmittance, i.e., a low weight, in a region that has no effect on the quality of an image, which leads to a low weight of the radiation imaging apparatus. The reduction in the weight of the radiation imaging apparatus can reduce the workload of a user when carrying the radiation imaging apparatus to make settings for an object.

On the other hand, the technique of the publication of Japanese Patent Application Laid-Open No. 2004-294114 uses an attenuation member having a low radiation transmittance, i.e., a high weight, in a portion where a part with a high radiation transmittance is placed on the surface of the FPD opposite the side where radiation is incident. For example, if a compact part with a low radiation transmittance that helps reduce the weight of the radiation imaging apparatus brings about a higher radiation transmittance of a region, an attenuation member with a low radiation transmittance will be placed in the region, which results in difficulty in making the radiation imaging apparatus lighter.

SUMMARY OF THE INVENTION

The present invention is directed to providing a technique for reducing the weight of a radiation imaging apparatus while reducing an artifact due to backscattered radiation that occurs in a radiation image.

According to an aspect of the present invention, a radiation imaging apparatus that emits radiation generated by a radiation generating unit to an object and generates a radiation image based on the radiation transmitted through an object includes a radiation detection unit including a first surface on which a plurality of pixels, each configured to convert the radiation into an electric signal, is provided and a second surface opposite the first surface, a plurality of parts provided on the second surface side with respect to the radiation detection unit, and an attenuation member provided the second surface side with respect to the radiation detection unit and configured to attenuate backscattered radiation incident on the radiation detection unit from the second surface side. The attenuation member includes a material having a radiation transmittance higher than a radiation transmittance of any of the plurality of parts, covers an end portion of an outline of the part that overlaps the radiation detection unit in orthogonal projection onto the second surface, and has an area smaller than an area of the radiation detection unit.

Further features of the present invention will become apparent from the following description of exemplary embodiments with reference to the attached drawings.

DESCRIPTION OF THE EMBODIMENTS

Some exemplary embodiments to which the present invention is applied will be described below in detail with reference to the attached drawings.

The following exemplary embodiments do not limit the invention according to the appended claims. Although a plurality of features will be described in the exemplary embodiments, some embodiments may not use all the features for implementing the invention, and other embodiments may use any combination of features. Further, in the attached drawings, like numbers refer to like components, and a redundant description will be omitted. Although the term "radiation" can typically represent an X-ray, it also can represent another type of radiation (e.g., an α-ray, a β-ray, or a γ-ray).

Figure 1:
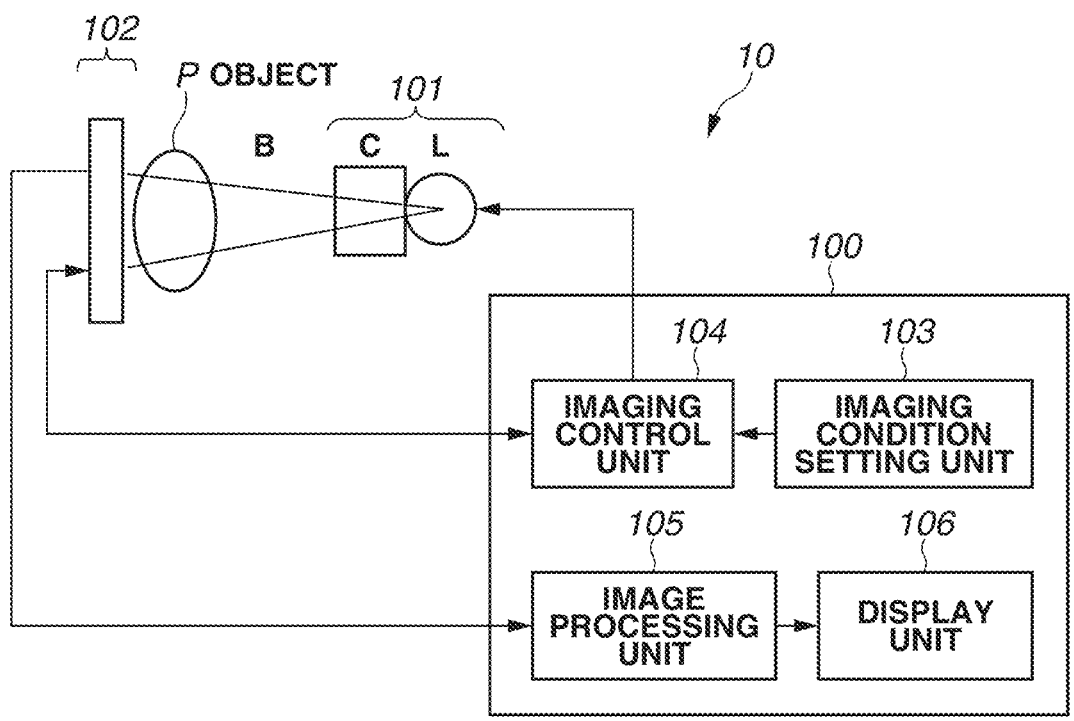
FIG. 1 is a diagram illustrating the configuration of a radiation imaging system according to a first exemplary embodiment.

FIG. 1 illustrates the overall configuration of a radiation imaging system 10 according to a first exemplary embodiment of the present invention. The radiation imaging system 10 includes a control apparatus 100, a radiation generating apparatus 101, and a radiation imaging apparatus 102. The control apparatus 100 includes an imaging condition setting unit 103, an imaging control unit 104, an image processing unit 105, and a display unit 106. As the control apparatus 100, a general-purpose computer including a central processing unit (CPU), a main storage device, an auxiliary storage device, and a display device can be suitably used. Computer-executable instructions (program code) can be stored in the storage devices, executed by the CPU, and results thereof displayed by the display device, thereby carrying out the functions of the units of the control apparatus 100.

The radiation generating apparatus 101 emits a radiation beam B towards an object P. The radiation generating apparatus 101 includes a tubular lamp L that generates radiation, a collimator C that regulates the spread angle of the beam of the generated radiation, and a radiation dose measuring device attached to the collimator.

The radiation imaging apparatus 102 generates a radiation image based on the radiation emitted from the radiation generating apparatus 101 and transmitted through the object P. The generated radiation image is transmitted to the image processing unit 105. The radiation imaging apparatus 102 also transmits information regarding the detected dose of radiation to the imaging control unit 104. The internal structure of the radiation imaging apparatus 102 will be described in detail with reference to FIGS. 2A and 2B.

The imaging condition setting unit 103 includes an imaging condition input unit for an operator to input imaging conditions such as a tube voltage, a tube current, and an imaging target part, and the imaging conditions input by the operator are transmitted to the imaging control unit 104. Based on the input imaging conditions, the imaging control unit 104 controls the radiation generating apparatus 101, the radiation imaging apparatus 102, and the image processing unit 105.

The image processing unit 105 performs image processing such as an offset correction process, a gain correction process, and a noise reduction process on the radiation image received from the radiation imaging apparatus 102. The image processing unit 105 transmits the radiation image subjected to the image processing to the display unit 106. As the display unit 106, a general-purpose display is used. The display unit 106 outputs image information transmitted from the image processing unit 105.

Figure 2A:
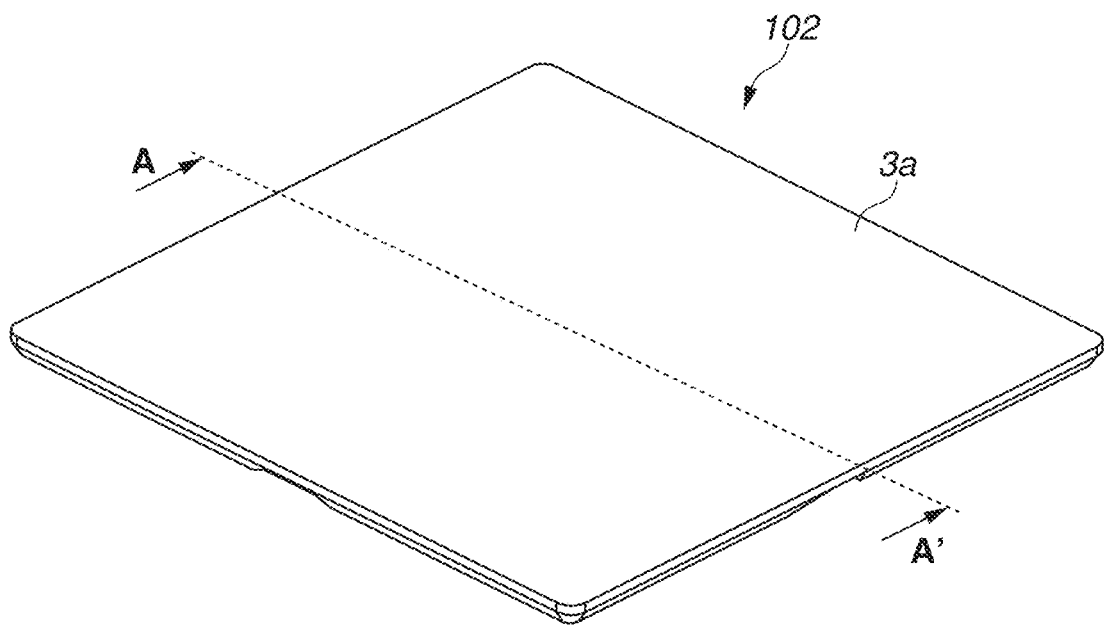
FIGS. 2A and 2B illustrate the configuration of a radiation imaging apparatus according to the first exemplary embodiment.
Figure 2B:
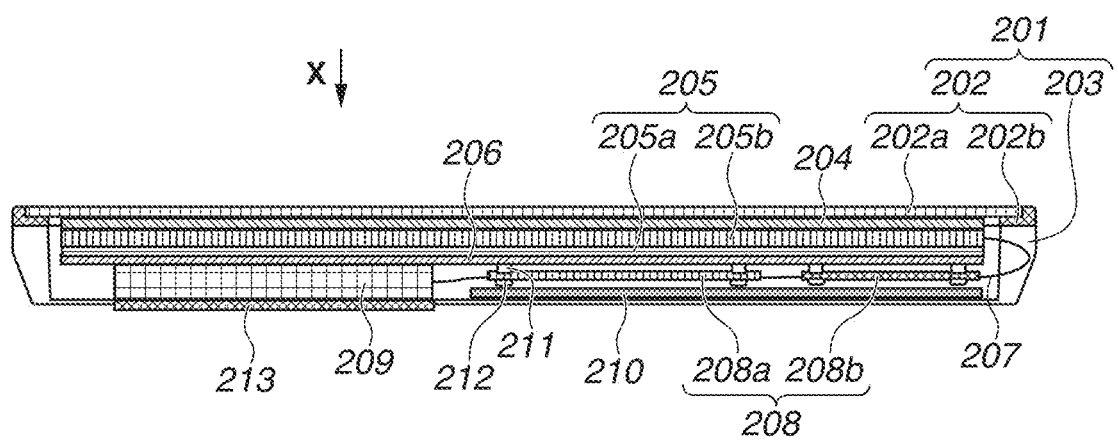

FIGS. 2A and 2B illustrate the configuration of the radiation imaging apparatus 102 according to the present exemplary embodiment. FIG. 2A is an external perspective view of the radiation imaging apparatus 102 as viewed in a direction of the incident surface 3a of the radiation imaging apparatus 102. FIG. 2B is a cross-sectional view of the radiation imaging apparatus 102 as seen in the direction perpendicular to an arrow X. The cross-sectional view is obtained by cutting the radiation imaging apparatus 102 along a line A-A' illustrated in FIG. 2A. The arrow X in FIG. 2B schematically indicates the direction of radiation incident on the surface 3a of radiation imaging apparatus 102.

The radiation imaging apparatus 102 has an approximately cuboid shape, and a housing 201 contains parts included in the radiation imaging apparatus 102. The housing 201 includes a front surface cover 202 including a breast pad portion 202a and a frame portion 202b, a back surface cover 203, and a removable cover 213 of a secondary battery 209.

The breast pad portion 202a is a plate-like member disposed at the surface of the housing 201 on which the radiation is incident. Since there are cases where load is applied to the radiation imaging apparatus 102 when the radiation imaging apparatus 102 is used in imaging, a member having a high rigidity is suitable as the breast pad portion 202a. Since the breast pad portion 202a is a surface on which the radiation from the radiation generating apparatus 101 is incident, a material having a high radiation transmittance is suitable for the breast pad portion 202a.

From these viewpoints, for example, carbon-fiber-reinforced plastic (CFRP) is used for the breast pad portion 202a. For the frame portion 202b located in the periphery of the breast pad portion 202a, magnesium alloy is used.

The back surface cover 203 is a plate-like member disposed at the surface opposite the radiation incident surface of the housing 201. As described above, since there are cases where load is applied to the radiation imaging apparatus 102, a member having a high rigidity is suitable as the back surface cover 203. To prevent reflection of the radiation in the housing 201, a material having a high radiation transmittance is also suitable for the back surface cover 203. From these viewpoints, for example, CFRP is used for the back surface cover 203.

In the housing 201, a shock absorption sheet 204, a radiation detection unit 205, and a base 206 are laminated in this order from the incident surface of the radiation. The shock absorption sheet 204 protects the radiation detection unit 205 from a shock received from outside the housing 201.

The radiation detection unit 205 is a flat-panel detector (FPD) including a scintillator layer 205b composed of a plurality of crystals of a scintillator that converts the wavelength of the radiation into that of light that can be sensed by the photoelectric conversion elements, on a plurality of pixels 205a, each of which includes a photoelectric conversion element and which is disposed in a two-dimensional array. The radiation emitted from the radiation generating apparatus 101 is converted into light by the scintillator layer 205b, and the light is further converted into electric signals by the photoelectric conversion elements of the plurality of pixels 205a. The electric signals from the plurality of pixels 205a are read by a driving circuit and a reading circuit, thereby generating a radiation image.

In the following description, the surface of the radiation detection unit 205 on which the plurality of pixels 205a is provided is referred to as a "first surface", and the surface opposite the first surface is referred to as a "second surface".

The radiation detection unit 205 is connected to a control board 208 via a flexible circuit board 207. The control board 208 (208a-208b) includes a driving circuit and a reading circuit. The reading circuit controls driving signals for reading the electrical signals from the photoelectric conversion elements.

The base 206 is a flat plate-like member for supporting the radiation detection unit 205 and other components. On the surface of the base 206 closer to the radiation incident surface, the radiation detection unit 205 is placed. On the surface of the base 206 opposite the surface where the radiation is incident, the control board 208, the secondary battery 209, and a wireless module and an antenna unit that are not illustrated are provided and supported by the base 206. For example, the control board 208 (208a-208b) is attached to the base 206 by fastening members (e.g., bolts) 212. On the surface opposite the surface of the base 206 closer to the surface where the radiation is incident, unevenness (staggered levels) may be formed by spacers 211 for supporting various parts at different distance from base 206. In view of a need to ensure rigidity, a reduction in weight, and reduce the influence of electrical noise, magnesium alloy is suitable for the base 206.

The secondary battery 209 supplies power for driving electronic components such as the radiation detection unit 205, control board 208, and the wireless module and antenna unit, among others. The wireless module and the antenna unit function as a wireless communication unit that wirelessly transmits image signals to an external apparatus.

An attenuation member 210 is provided to attenuate backscattered radiation incident on the radiation detection unit 205. The "backscattered radiation" refers to a component obtained as follows. When part of the radiation emitted to the radiation detection unit 205 passes through the radiation detection unit 205 or the irradiation field of the radiation is wider than the radiation detection unit 205, the radiation is reflected by one or more structures opposite the surface where the radiation is incident on the radiation detection unit 205, and the reflected radiation is incident again as backscattered radiation on the radiation detection unit 205. The backscattered radiation will be described in detail with reference to FIG. 3. For the attenuation member 210, a material that absorbs radiation, such as bismuth, lead, stainless steel (SUS), iron, or tungsten, or alloys thereof can be used.

The attenuation member 210 is a member for attenuating backscattered radiation incident on the radiation detection unit 205. Since the radiation is reflected by one or more structures opposite to the surface where the radiation is incident on the radiation detection unit 205, the attenuation member 210 is provided on the second surface side of the radiation detection unit 205. For example, in one embodiment, the attenuation member 210 is provided between the radiation detection unit 205 and the base 206. In other embodiments, the attenuation member 210 is provided inside and/or outside the back surface cover 203 of the housing 201. The attenuation member can be bonded to an inner surface or an outer surface of the housing through an adhesive layer. The present invention, however, is not limited to this. For example, in another embodiment, the attenuation member 210 is provided between the control boards 208a-208b and inside the back surface cover 203 of the housing 201, as shown in FIG. 2B. The layout that the attenuation member 210 is positioned closer to the second surface than the first surface of the radiation detection unit 205 is not shown.

Figure 3:
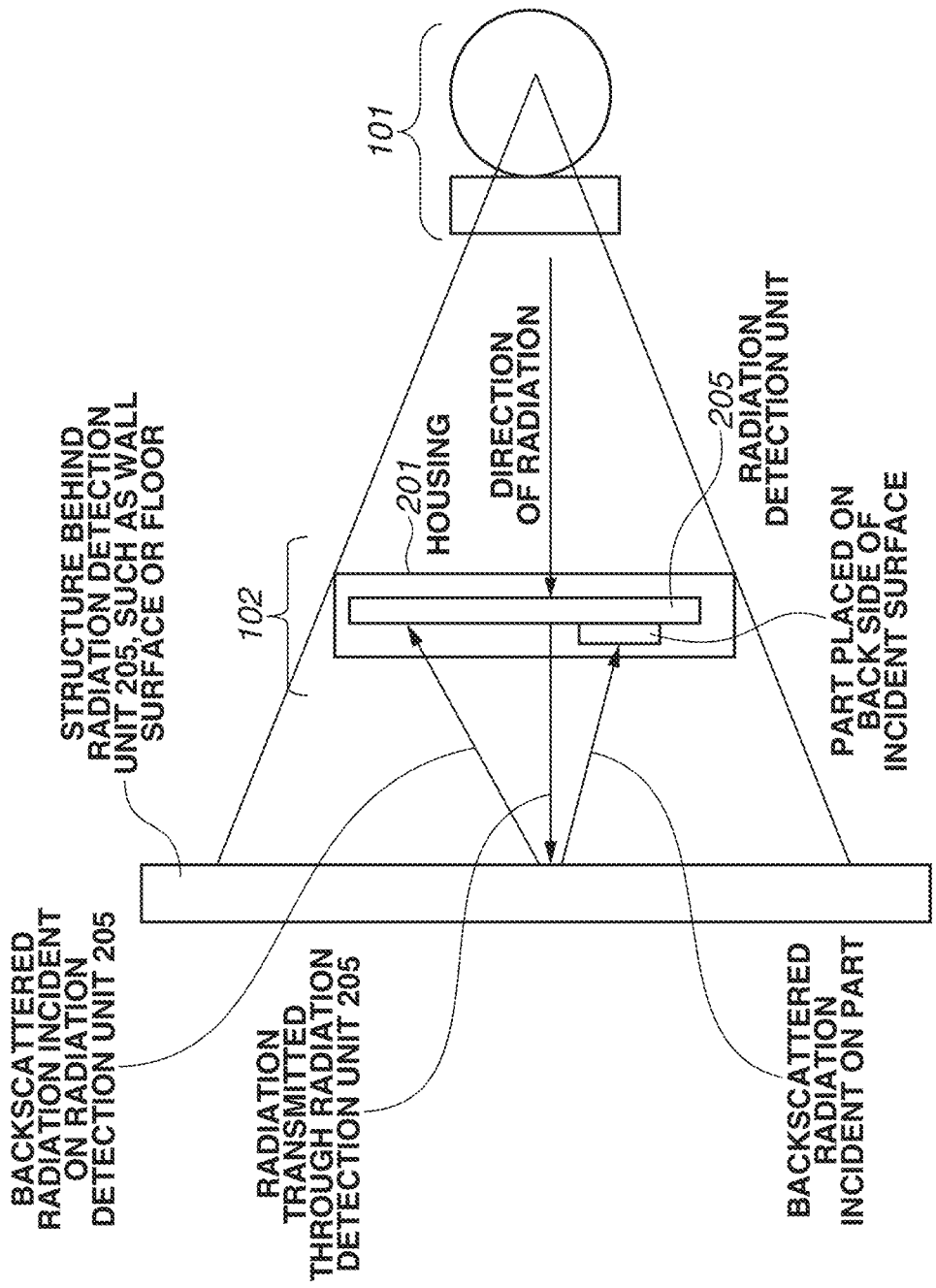
FIG. 3 is a schematic diagram illustrating backscattered radiation according to the first exemplary embodiment.

Next, with reference to FIG. 3, backscattered radiation will be described. FIG. 3 illustrates the state of backscattered radiation regarding the radiation generating apparatus 101 and the radiation imaging apparatus 102 in FIG. 1. Radiation emitted from the radiation generating apparatus 101 passes through the object P and is incident on the radiation detection unit 205 inside the radiation imaging apparatus 102.

Part of the radiation incident on the radiation detection unit 205 passes through the scintillator layer 205b of the radiation detection unit 205 without being absorbed by the scintillator layer 205b, is reflected and scattered by a structure such as a wall surface or a floor on the back surface side of the radiation imaging apparatus 102, and is incident again from the structure on the back surface side of the radiation detection unit 205. This backscattered radiation incident from the structure on the back surface side includes backscattered radiation attenuated by an attenuation part of the radiation imaging apparatus 102 installed on the back surface side and backscattered radiation incident on a phosphor. The difference in radiation transmittance between the portion where the attenuation part is present and the portion where the attenuation part is not present causes an unexpected appearance of the attenuation part in a radiation image, i.e., the occurrence of an artifact.

If the attenuation member 210 is provided to cover the entire surface of the radiation detection unit 205 to shield the radiation detection unit 205 from the backscattered radiation, the absolute amount of backscattered radiation incident on the radiation detection unit 205 can be decreased, which reduces an artifact. The attenuation member 210 provided on the entire surface will increase the weight of the radiation imaging apparatus 102. In the nature of the apparatus, the radiation imaging apparatus 102 is used by a user carrying the radiation imaging apparatus 102 in many tasks such as making settings for an object. Thus, it is suitable to reduce the weight of the radiation imaging apparatus 102 wherever possible.

Thus, in the present invention, such an artifact due to an unexpected appearance of an attenuation part resulting from backscattered radiation generated outside the housing 201 of the radiation imaging apparatus 102 is reduced while the weight of the radiation imaging apparatus 102 is reduced with an attenuation member smaller than the area of the radiation detection unit 205.

Figure 4A:
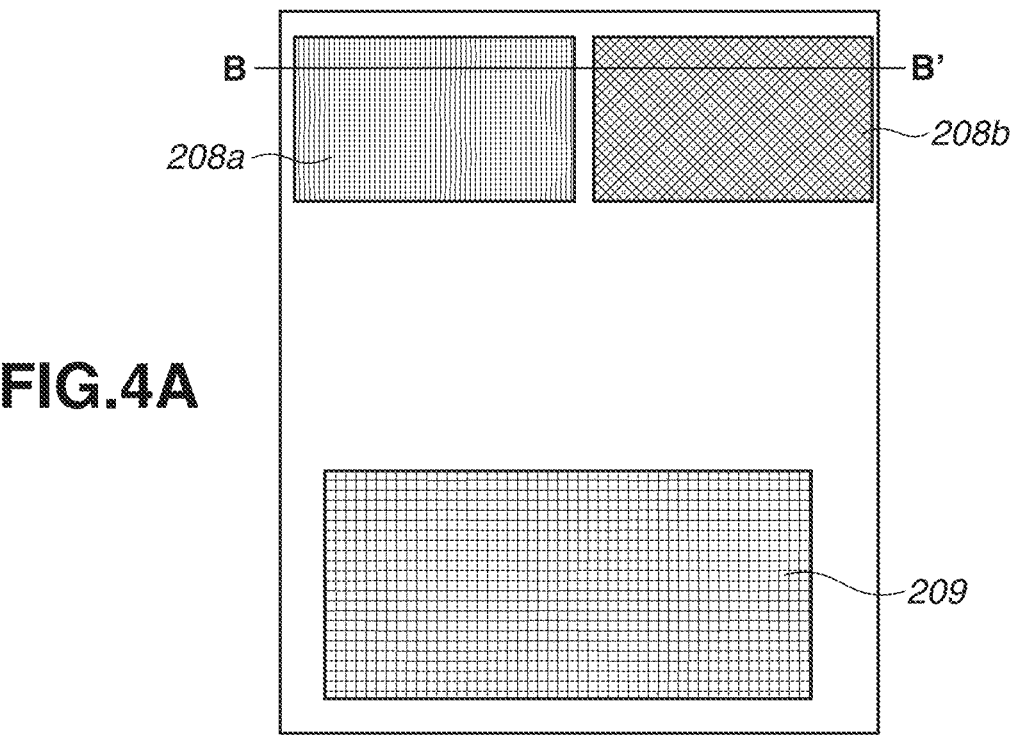
FIGS. 4A and 4B are schematic diagrams illustrating arrangement of an attenuation member according to the first exemplary embodiment.
Figure 4B:
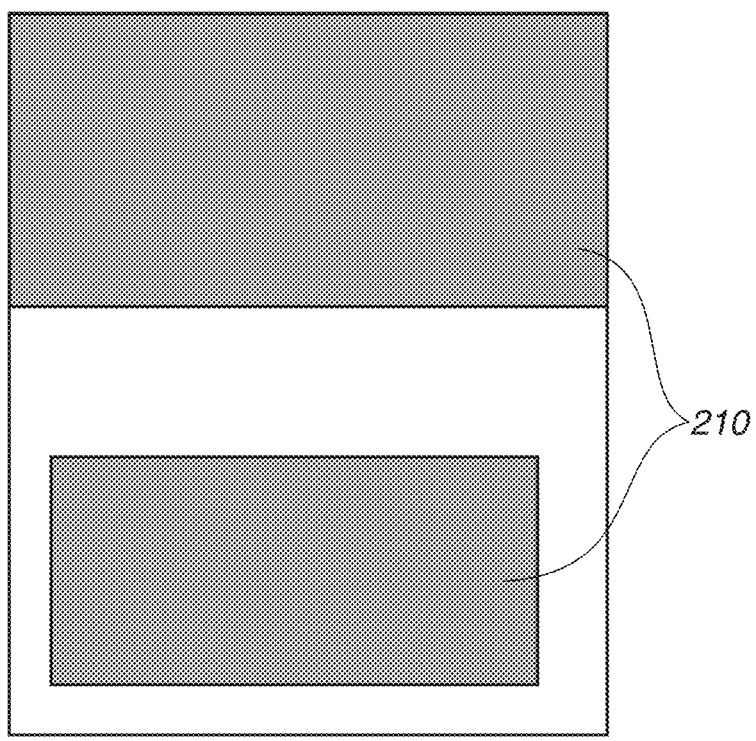

FIGS. 4A and 4B are diagrams illustrating a configuration of the radiation imaging apparatus 102 according to an exemplary embodiment in a simplified manner. FIG. 4A illustrates the side opposite the surface where radiation is incident (the arrow X in FIG. 2) on the radiation imaging apparatus 102 without the attenuation member 210. FIG. 4B illustrating the attenuation member 210 added to FIG. 4A. In the radiation imaging apparatus 102 illustrated in FIG. 4A, a control board 208a, a control board 208b, and the secondary battery 209 are provided.

This layout causes a great difference in the amount of incident backscattered radiation between the end portion of the outline of each of these parts and the portion where the part is not present in the in-plane direction of the second surface of the radiation detection unit 205. The portions with such a great difference in the amount of backscattered radiation cause as an artifact in a radiation image.

In the present exemplary embodiment, the attenuation member 210 is provided to cover the end portion of the outline of a part on the second surface side of the radiation detection unit 205 as an unexpected appearance reduction target in orthogonal projection onto the second surface of the radiation detection unit 205. The attenuation member 210 has a radiation transmittance higher than that of the part as the unexpected appearance reduction target.

This configuration allows reduction of an artifact by the reduction in the difference in the amount of backscattered radiation reaching the second surface of the radiation detection unit 205, the difference of which occurs between the end portion of the outline of the part as the unexpected appearance reduction target and the portion where the part is not present.

Figure 5A:
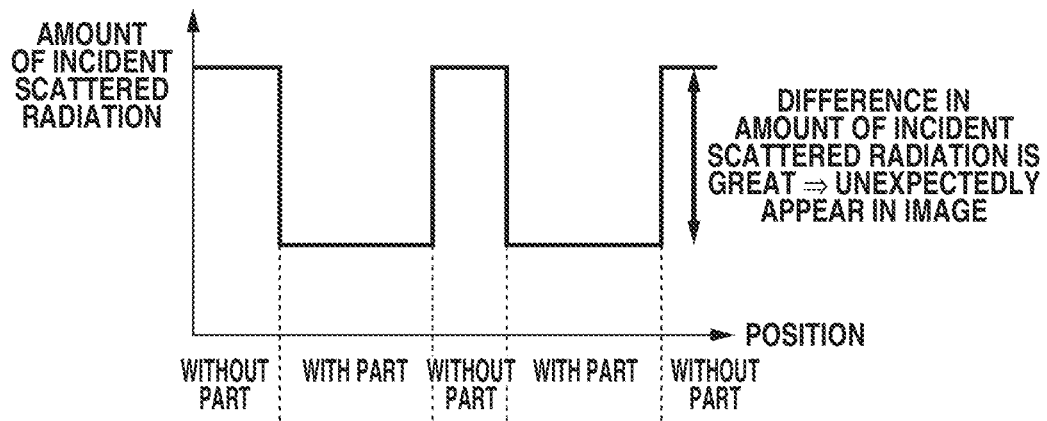
FIGS. 5A and 5B illustrate relationships between positions in FIGS. 4A and 4B and amounts of incident scattered radiation according to the first exemplary embodiment.
Figure 5B:
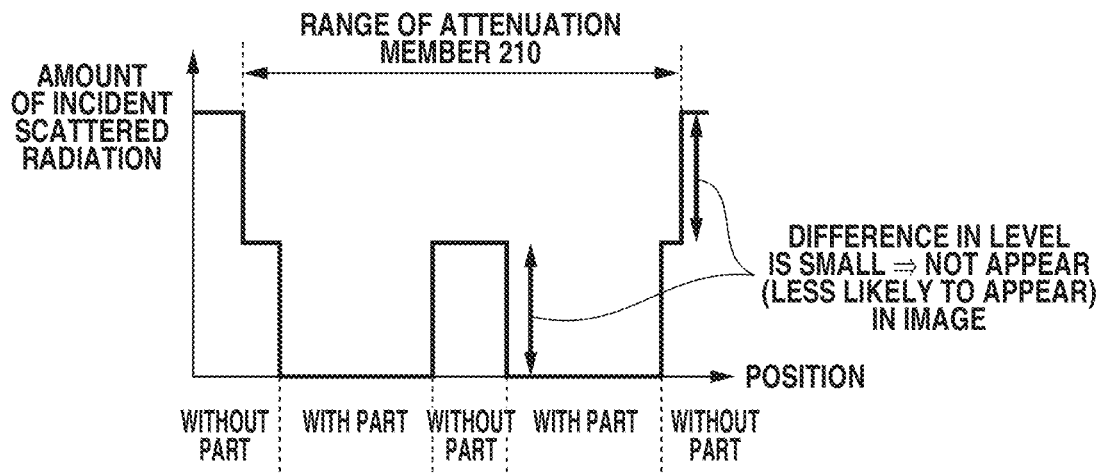

The following is a description with reference to FIGS. 4A, 4B, 5A, and 5B. FIGS. 5A and 5B illustrate the amount of scattered radiation incident on the radiation detection unit 205 at the position of a line B-B' in FIG. 4A. FIG. 4A illustrates regions where parts (the control boards 208a and 208b in FIG. 4A) are not provided and regions where the parts are provided along the line B-B' on the surface opposite the radiation incident surface on the radiation detection unit 205 in the radiation imaging apparatus 102. FIGS. 5A and 5B illustrate the amount of incident scattered radiation on each region.

FIG. 5A corresponds to a case where the attenuation member 210 is not provided in FIG. 4A. FIG. 5B corresponds to a case where the attenuation member 210 is provided in FIG. 4B. In FIG. 5A, a great difference occurs in the amount of incident scattered radiation between the regions where the parts are not provided and the regions where the parts are provided, whereby the parts unexpectedly appear as a source of an artifact. On the other hand, in FIG. 5B, which corresponds to the case where the attenuation member 210 is provided, the attenuation member 210 creates regions covered by the parts and the attenuation member 210, regions covered by the attenuation member 210 alone, and regions covered by neither the parts nor the attenuation member 210.

The differences in the amount of incident scattered radiation between the regions in FIG. 5B are smaller than the difference between the regions where the parts are not provided and the regions where the parts are provided without the attenuation member 210. Thus, the parts are less likely to unexpectedly appear, allowing the reduction of an artifact.

The attenuation member 210 has a material with a radiation transmittance higher than those of parts as unexpected appearance reduction targets. This is because the radiation transmittance of the attenuation member 210 lower than those of the parts as the unexpected appearance reduction targets causes the parts to unexpectedly appear. In FIG. 4B, the attenuation member 210 is provided to cover the control board 208a, the control board 208b, and the secondary battery 209. As described above with reference to FIGS. 5A and 5B, the differences in the amount of backscattered radiation between these regions are small as compared with the case without the attenuation member 210. Thus, the parts are less likely to unexpectedly appear on the resulting image, allowing the reduction of an artifact.

In the above description of FIG. 4B, the parts as the unexpected appearance reduction targets are the control board 208 and the secondary battery 209, but an object to cover is not limited to these. For example, the attenuation member 210 may be provided to cover the end portion of the outline of an uneven portion provided in the base 206, an antenna for communication of the radiation imaging apparatus 102, a cable for connecting various electric parts, or a fastening member for fixing various parts.

The thickness of the end portion of the outline of the attenuation member 210 may be continuously changed. This can reduce the difference in the amount of backscattered radiation reaching the second surface of the radiation detection unit 205 on the end portion of the attenuation member 210, making the shape of the outline of the attenuation member 210 less likely to unexpectedly appear in a radiation image.

The attenuation member 210 may be attachable to and detachable from the radiation imaging apparatus 102.

The above described configuration makes it easy to arrange the attenuation member 210 at an appropriate position after viewing the state of unexpected appearance in an actually captured radiation image. The configuration that the attenuation member 210 is attachable to and detachable from the radiation imaging apparatus 102 also makes it easy to change the material of the attenuation member 210 based on the state of the unexpected appearance in the radiation image.

A second exemplary embodiment of the present invention will be described. The second exemplary embodiment is different from the first exemplary embodiment in that the attenuation member 210 covers the end portion of the outline of a part as an unexpected appearance reduction target, not the entire part.

Figure 6A:
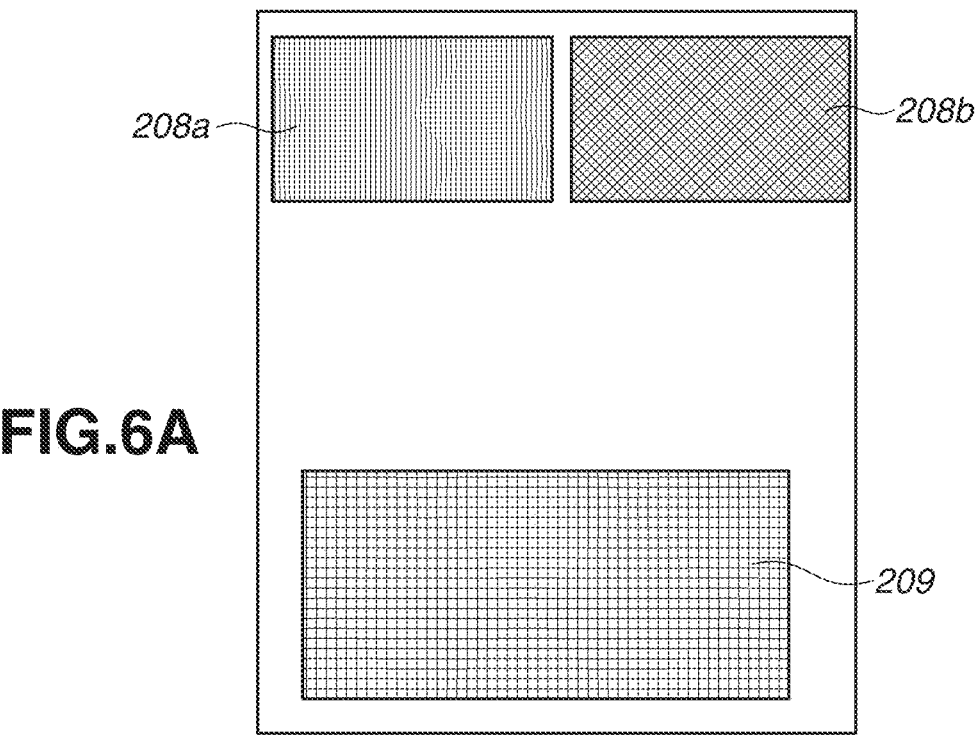
FIGS. 6A and 6B are schematic diagrams illustrating arrangement of an attenuation member according to a second exemplary embodiment.
Figure 6B:
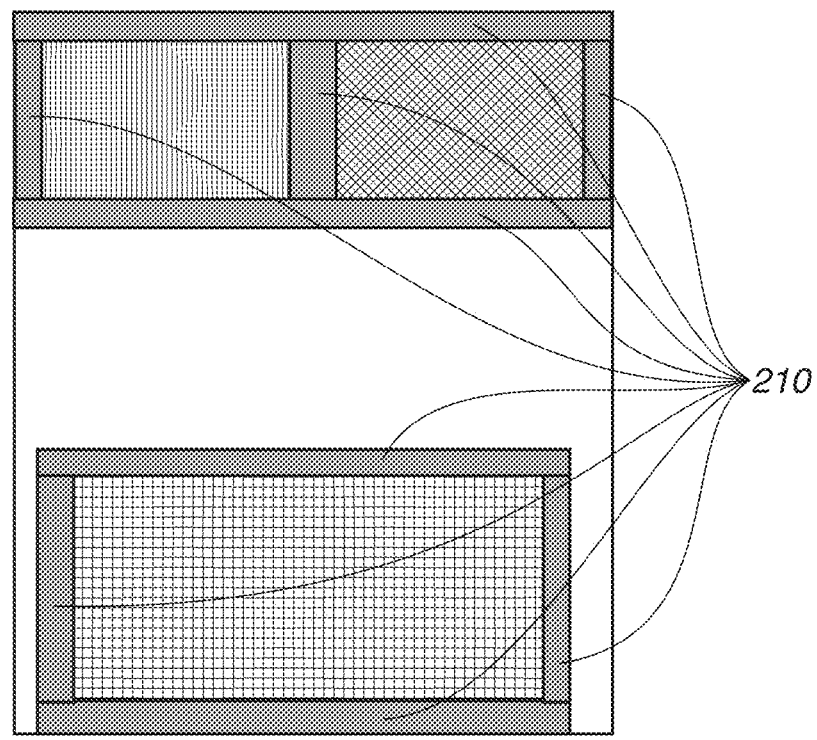

FIGS. 6A and 6B illustrate the configuration of the radiation imaging apparatus 102 according to the present exemplary embodiment in a simplified manner. FIG. 6A illustrates the side opposite the radiation incident surface of the radiation imaging apparatus 102 without the attenuation member 210. FIG. 6B illustrates the attenuation member 210 is added to the radiation imaging apparatus 102 of FIG. 6A.

In the present exemplary embodiment, the control board 208a, the control board 208b, and the secondary battery 209 are provided in the radiation imaging apparatus 102, as parts as unexpected appearance reduction targets, and the attenuation member 210 is placed along the end portion of the outline of each of the parts. The attenuation member 210 is arranged as illustrated in FIG. 6B, which reduces the area of the attenuation member 210 compared with that in the first exemplary embodiment. Thus, that configuration allows a reduction of the weight of the radiation imaging apparatus 102.

A third exemplary embodiment of the present invention will be described. In the present exemplary embodiment, the unexpected appearance of the end portion of the attenuation member 210 is reduced.

To quantitatively evaluate the amount of artifact, let A denote the average pixel value of a region where a part unexpectedly appears, and B denote the average pixel value of a region where a part near the part does not appear, the difference in shade can be obtained by the following formula (1).

$$\text{The difference in shade} = (B-A)/A \quad (1)$$

Figure 7:
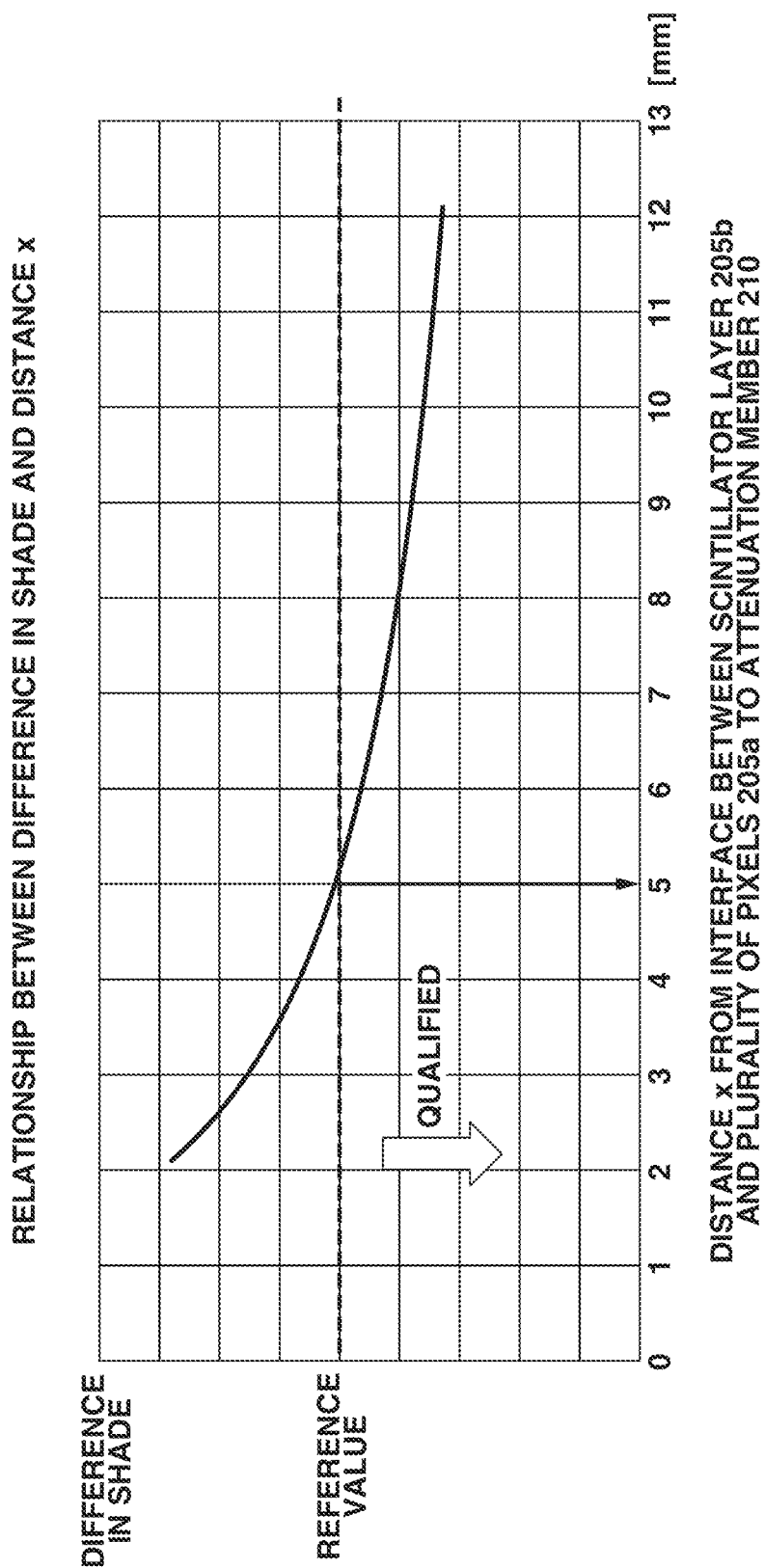
FIG. 7 illustrates a relationship between differences in shade and distances to a blocking member according to a third exemplary embodiment.

FIG. 7 illustrates a graph indicating the evaluation of the relationship between the difference in shade and a distance x, where x is a distance from the interface between each of the plurality of pixels 205a and the scintillator layer 205b to the attenuation member 210 disposed in a region covering the control board 208a in orthogonal projection onto the detection surface. As illustrated in FIG. 7, as the distance x is greater, the difference in shade is smaller. This is because with a great distance x backscattered radiation goes around the periphery of the attenuation member 210 and reaches the scintillator layer 205b, which prevents a clear appearance of the end portion of the attenuation member 210.

A dotted line illustrated as a reference value indicates a reference value for the difference in shade obtained from a plurality of radiation images and considered not to affect the actual use of the images. The intersection between the reference value and data about the difference in shade corresponds to 5 mm. From this result, it is understood that if the distance from the interface between the scintillator layer 205b and each of the plurality of pixels 205a to the radiation attenuation member 210 is greater than or equal to 5 mm, the difference in shade falls under the reference value. To obtain a more suitable image, the distance may be greater than or equal to 8 mm.

As described above, in the present exemplary embodiment, to reduce the unexpected appearance of the attenuation member 210, the attenuation member 210 is provided away from the radiation detection unit 205. This arrangement allows reduction of the amount of artifact due to backscattered radiation using the attenuation member 210 while also reducing the occurrence of an artifact due to the attenuation member 210.

According to the present invention, a radiation imaging apparatus can be provided that reduces an artifact due to backscattered radiation generated behind the radiation imaging apparatus with a reduced weight of the radiation imaging apparatus.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2021-138848, filed Aug. 27, 2021, and No. 2021-138849, filed Aug. 27, 2021, which are hereby incorporated by reference herein in their entirety.

What is claimed is:

1. A radiation imaging apparatus that emits radiation generated by a radiation generating unit to an object and generates a radiation image based on the radiation transmitted through the object, the radiation imaging apparatus comprising:
   a radiation detection unit including a first surface and a second surface opposite the first surface, the first surface including a plurality of pixels configured to convert the radiation into an electric signal;
   a circuit board having a plurality of parts and provided on the second surface side with respect to the radiation detection unit such that the second surface side has a first region on which a center of the circuit board is provided and a second region on which an outline of the circuit board is provided; and
   an attenuation member provided on the second surface side with respect to the radiation detection unit and configured to attenuate backscattered radiation incident on the radiation detection unit from the second surface side,
   wherein the attenuation member includes a material having a radiation transmittance higher than a radiation transmittance of any of the plurality of parts, does not cover the first region but covers the second region, and has an area smaller than an area of the radiation detection unit.

2. The radiation imaging apparatus according to claim 1, wherein the attenuation member is provided away from the second surface of the radiation detection unit.

3. A radiation imaging apparatus that emits radiation generated by a radiation generating unit to an object and generates a radiation image based on the radiation transmitted through the object, the radiation imaging apparatus comprising:
   a radiation detection unit including a first surface on which a plurality of pixels, each configured to convert the radiation into an electric signal, is provided and a second surface opposite the first surface;
   a plurality of parts provided on the second surface side of the radiation detection unit such that the second surface side has a first region on which none of the parts is provided and a second region on which at least one part of the plurality of parts is provided; and
   an attenuation member provided on the second surface side of the radiation detection unit and configured to attenuate radiation incident on the attenuation member to reduce appearance of any of the plurality of parts in a radiation image,
   wherein the attenuation member does not cover the first region but covers the second region, and
   wherein in orthogonal projection onto the second surface, an area of the attenuation member is smaller than an area of the radiation detection unit and the attenuation member is provided away from the second surface of the radiation detection unit so that the at least one part of the plurality of parts is positioned therebetween.

4. The radiation imaging apparatus according to claim 3, wherein the plurality of parts includes a part composed of a plurality of component parts for forming the part, and
   wherein the attenuation member covers an end portion of an outline of each of the plurality of component parts that overlaps the radiation detection unit in orthogonal projection onto the second surface.

5. The radiation imaging apparatus according to claim 3, wherein the plurality of parts includes a control board configured to read a signal from the radiation detection unit, and
   wherein the attenuation member covers an end portion of an outline of the control board that overlaps the radiation detection unit in orthogonal projection onto the second surface.

6. The radiation imaging apparatus according to claim 3, wherein the plurality of parts includes a secondary battery configured to supply power to the radiation imaging apparatus, and
   wherein the attenuation member covers an end portion of an outline of the secondary battery that overlaps the radiation detection unit in orthogonal projection onto the second surface.

7. The radiation imaging apparatus according to claim 3, wherein the plurality of parts includes an antenna for the radiation imaging apparatus to communicate with an external apparatus, and
   wherein the attenuation member covers an end portion of an outline of the antenna that overlaps the radiation detection unit in orthogonal projection onto the second surface.

8. The radiation imaging apparatus according to claim 3, wherein the plurality of parts includes a base configured to support the radiation detection unit on the second surface of the radiation detection unit, and
   wherein the attenuation member covers an end portion of unevenness of the base that overlaps the radiation detection unit in orthogonal projection onto the second surface.

9. The radiation imaging apparatus according to claim 3, wherein the plurality of parts includes a fastening member configured to fasten a part included in the radiation imaging apparatus, and
   wherein the attenuation member covers an end portion of an outline of the fastening member that overlaps the radiation detection unit in orthogonal projection onto the second surface.

10. The radiation imaging apparatus according to claim 3, wherein the plurality of parts includes a cable connected to a part included in the radiation imaging apparatus, and
    wherein the attenuation member covers an outline of the cable that overlaps the radiation detection unit in orthogonal projection onto the second surface.

11. The radiation imaging apparatus according to claim 3, wherein a thickness of an end portion of an outline of the attenuation member continuously changes.

12. The radiation imaging apparatus according to claim 3, wherein the attenuation member is attachable to and detachable from the radiation imaging apparatus.

13. The radiation imaging apparatus according to claim 3, wherein the attenuation member includes at least any one of bismuth, lead, stainless steel (SUS), iron, or tungsten.

14. The radiation imaging apparatus according to claim 3, further comprising a housing containing the radiation detection unit and the plurality of parts, wherein a surface of the housing opposite a surface on which the radiation is incident includes carbon-fiber-reinforced plastic (CFRP).

15. The radiation imaging apparatus according to claim 3, further comprising a housing configured to enclose the radiation detection unit and the plurality of parts,
wherein the attenuation member is provided outside the housing, on an outer surface of the housing such that the attenuation member overlaps the radiation detection unit or at least one of the plurality of parts in orthogonal projection onto the second surface.

16. The radiation imaging apparatus according to claim 3, further comprising a housing containing the radiation detection unit and the plurality of parts,
wherein the attenuation member is provided inside the housing, on an inner surface of the housing such that the attenuation member overlaps the radiation detection unit or at least one of the plurality of parts in orthogonal projection onto the second surface.

17. The radiation imaging apparatus according to claim 3, further comprising a housing containing the radiation detection unit and the plurality of parts,
wherein the attenuation member is bonded to the housing through an adhesive layer.

18. The radiation imaging apparatus according to claim 3, wherein each of the plurality of pixels includes a photoelectric conversion element, and the radiation detection unit includes a scintillator configured to convert the radiation into light that can be sensed by the photoelectric conversion element.

19. A radiation imaging system comprising:
the radiation imaging apparatus according to claim 3; and
an image processing unit configured to process radiation detected by the radiation imaging apparatus as a radiation image.

* * * * *